United States Patent [19]

Calabretta et al.

[11] Patent Number: 5,817,783
[45] Date of Patent: Oct. 6, 1998

[54] DR-NM23 AND COMPOSITIONS, METHODS OF MAKING AND METHODS OF USING THE SAME

[75] Inventors: Bruno Calabretta; Donatella Venturelli; Robert V. Martinez, all of Philadelphia, Pa.

[73] Assignee: Thomas Jefferson University, Philadelphia, Pa.

[21] Appl. No.: 667,023

[22] Filed: Jun. 20, 1996

[51] Int. Cl.$^6$ .................................................. C07H 21/04
[52] U.S. Cl. .................... 536/23.1; 536/23.5; 536/24.31; 435/320.1; 435/252.3; 435/254.11; 435/254.2; 514/44
[58] Field of Search ................................ 536/23.1, 23.5, 536/24.31; 435/320.1, 240.2, 252.3, 254.11, 240.4, 254.2; 514/44

[56] References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/172.3 |

OTHER PUBLICATIONS

Arad, G. et al., "Use of Reconstituted Sendai Virus Envelopes for Fusion–Mediated Microinjection of Double-Stranded RNA: Inhibition of Protein Synthesis in interferon–Treated Cells", *Biochimica et Biophysica Acta*, 1986, 859, 88–94.

Capecchi, M.R, "Altering the Genome by Homologous Recombination", *Science*, 1989, 244, 1288–1292.

Gong, J. et al., "A Selective Procedure for DNA Extraction from Apoptotic Cells Applicable for Gel Electrophoresis and Flow Cytometry", *Anal. Biochem.*, 1994, 218, 314–319.

Groffen, J. et al., "Philadelphia Chromosomal Breakpoints are Clustered within a Limited Region, bcr, on Chromosome 22", *Cell*, 1984, 36, 93–99.

Hailat, N. et al., "High Levels of p19/nm23 Protein in Neuroblastoma are Associated with Advanced Stage Disease and with N–myc Gene Amplication", *J. Clin. Invest.*, 1991, 88, 341–345.

Igawa, M. et al., "High Levels of nm23 Expression are Related to Cell Proliferation in Human Prostate Cancer", *Cancer Research*, 1994, 54, 1313–1318.

Kantarjian, H.M. et al., "Chronic Myelogenous Leukemia: A Concise Update", *Blood*, 1993, 82(3), 691–703.

Keim, D. et al, "Proliferation–Related Expression of p19/nm23 Nucleoside Diphosphate Kinase", *J. Clin. Invest.*, 1992, 89, 919–924.

Leone, A. et al., "Evidence for nm23 RNA Overexpression, DNA amplification and Mutation in Aggressive Childhood Neuroblastomas", *Oncogene*, 1993, 8, 855–865.

Leone, A. et al., "Reduced Tumor Incidence, Metastatic Potential, and Cytokine Responsiveness of nm23–Transfected Melanoma Cells", *Cell*, 1991, 65, 25–35.

Li, P. et al., "Mice Deficient in IL–1β–Converting Enzyme are Defective in Production of Mature IL–1β and Resistant to Endotoxic Shock", *Cell*, 1995, 80, 401–411.

MacDonald, N.J. et al., "A Serine Phosphorylation of Nm23, and Not Its Nucleoside Diphosphate Kinase Activity, Correlates with Suppression of Tumor Metastatic Potential", *J. Biol. Chem.*, 1993, 268(34), 25780–25789.

Mandai, M. et al., "Expression of Metastasis–Related nm23–H1 and nm23–H2 Genes in Ovarian Carcinomas: Correlation with Clinicopathology, EGFR, c–erbB–2, and c–erbB–3 Genes, and Sex Steroids Receptor Expression", *Cancer Res.*, 1994, 54, 1825–1830.

Nakamori, S. et al., "Expression of Nucleoside Diphosphate Kinase/nm23 Gene Product in Human Pancreatic Cancer: an Association with Lymph Node Metastasis and Tumor Invastion", *Clin. Exp. Metastasis*, 1993, 11, 151–158.

Okabe–Kado, J. et al., "Identity of a Differentiation Inhibiting Factor for Mouse Myeloid Leukemia Cells with NM23/Nucleoside Diphosphate Kinase", *Biochem. And Biophys. Res. Comm.*, 1992, 182(3), 987–994.

Rosengard, A.M. et al., "Reduced Nm23/Awd Protein in Tumour Metastasis and Aberrant Drosophila Development," *Nature*, 1989, 342, 177–180.

Rowley, J.D., "Identification of the Constant Chromosome Regions Involved in Human Hemotologic Malignant Disease", *Science*, 1982, 216, 749–751.

Ruoslahti, E. et al., "New Perspectives in Cell Adhesion: RGD and Integrins", *Science*, 1987, 238, 491–497.

Stahl, J.A. et al., "Identification of a Second Human nm23 Gene, nm23–H2", *Cancer Res.*, 1991, 51, 445–449.

Ullrich, A. et al., "Insulin–Like Growth Factor I Receptor Primary Structure: Comparison with Insulin Receptor Suggests Structural Determinants that Define Functional Specificity", *EMBO J.*, 1986, 5(10), 2503–2512.

Wang, L. et al., "Mutation in the nm23 Gene is Associated with Metastasis in Colorectal Cancer", *Cancer Res.*, 1993, 53, 717–720.

Wide, L., "Solid Phase Antigen–Antibody Systems", *Radioimmunoassay Methods*, 1970, pp. 405–412.

Yamashiro, S. et al., "Alteration of nm23 Gene Expression During the Induced Differentiation of Human Leukemia Cell Lines", *Oncogene*, 1994, 9, 2461–2468.

(List continued on next page.)

*Primary Examiner*—Robert A. Wax
*Assistant Examiner*—Enrique D. Longton
*Attorney, Agent, or Firm*—Woodcock Washburn Kurtz Mackiewicz & Norris, LLP

[57] ABSTRACT

DR-nm23 protein is disclosed. A nucleotide sequence encoding the same and fragments thereof, recombinant expression vectors that comprise the nucleotide sequence, host cell comprising the recombinant expression vectors and methods of making DR-nm23 protein are disclosed. Oligonucleotide molecules comprising a nucleotide sequence complementary to a portion of the nucleotide sequence that encodes DR-nm23 and methods of using the same to inhibit DR-nm23 expression are disclosed. Isolated antibodies that bind to an epitope on DR-nm23 are disclosed. Methods of tracking the progress on chronic myelogenous leukemia and methods of detecting the onset of blast crisis phase in an individual with chronic myelogenous leukemia are disclosed.

15 Claims, No Drawings

OTHER PUBLICATIONS

Hemmerich et al. (1992) A Cromoglycate Binding Protein from Rat Mast Cells of a Leukemia Line Is a Nucleoside Diphosphate Kinase. Biochemistry 31, pp. 4574–4579.

Accession No. M91597 J05373 Hemmerich et al. (1992) Sprague–Dawley (p18–12d) RBL–NDP Kinase 18kDa subunit (p18) mRNA complete cds.

Kimura et al. (1990) Isolation and Characterization of a cDNA Clone Encoding Rat Nucleoside Disphosphate Kinase. J. Biol. Chem. 265 (26) pp. 15744–15749.

Accession No. M55331 J05588 Kinura et al. (1992) Rat Nucleoside Diphosphate Kimase mRNA, complete cds.

Accession No. U29656 Venturelli et al. (1996) Human DR nm–23 mRNA complete cds.

Venturelli et al. (1995) Overexpression of DR–nm23, a protein encoded by a member of the nm23 gene family, inhibits granulocyte differentiation and induces apoptosis in 32Dc13 myeloid cells. Proc. Natl. Acad. Sci. USA 92, pp. 7435–7439.

Accession No. H83355 Hillier et al. (1995) yv82f04.r1 Homo sapiens cDNA clone 249247.

DR-NM23 AND COMPOSITIONS, METHODS OF MAKING AND METHODS OF USING THE SAME

ACKNOWLEDGEMENT OF GOVERNMENT RIGHTS

This invention was made with Government support under Grant 46782 from the National Institutes of Health. The Government has certain rights in this invention.

CROSS REFERENCE TO RELATED APPLICATIONS

This application claims priority U.S. Provisional application 60/000,427 filed Jun. 22, 1995.

FIELD OF THE INVENTION

The invention relates to the identification and cloning of Dr-nm23, a gene related to nm-23. The invention relates to the isolated protein, the nucleic acid molecules that encode the protein, to related compositions including antibodies, probes, primers and antisense compositions, and to methods of making and using the same.

BACKGROUND OF THE INVENTION

Hematopoiesis is a regulated developmental cascade that generates at least eight distinct lineages that differentiate into mature blood cells. Central to the process are pluripotent stem cells which generate a hierarchy of developmental transients consisting of multipotent and unipotent progenitor cells. Since most mature blood cells have short lifespans, the continuous regeneration of multipotent and unipotent progenitors is essential to hematopoietic homeostasis.

Chronic myelogenous leukemia (CML) is a malignancy of the human hematopoietic stem cell characterized by the Philadelphia chromosome (Ph) and, at the molecular level, juxtaposition of 5' coding sequences of the breakpoint cluster region (bcr) gene on chromosome 22 and 3' coding sequences of the c-abl gene on chromosome 9. CML involves myeloid, erythroid, megakaryocytic, B- and sometimes T-lymphocyte lineages, but not marrow fibroblasts. The hallmarks of CML are threefold and include (1) the presence of the Ph chromosome, (2) a biphasic or triphasic course, (3) the heterogeneity of the disease among patients.

Clinically, CML presents initially as a chronic phase characterized by an increased number of immature myeloid precursor cells which retain the ability to terminally differentiate. With current therapeutic regimens, it usually progresses, 3–5 years after diagnosis, to an accelerated phase with a duration of 1–1.5 years and then into a blastic phase, characterized by growth advantage and differentiation arrest of CML blast cells. CML blast crisis is usually fatal within 3–6 months, irrespective of the treatment.

Although the prognostic factors associated with the disease process are better known than in the past, the molecular mechanisms by which the disorder progresses from the chronic phase to the terminal blast phase remain elusive. There is a need for molecular based prognostic indicators. There is a need to identify genes which are markers in the progress of CML from chronic to blast crisis phase. There is a need to identify genes which modulate the growth, metastatic members and differentiation of cells.

SUMMARY OF THE INVENTION

The invention relates to a substantially pure protein that have amino acid sequences shown in SEQ ID NO:2.

The invention relates to isolated nucleic acid molecules that comprise nucleic acid sequences that encode a protein that has an amino acid sequence shown in SEQ ID NO:2.

The invention relates to isolated nucleic acid molecules that comprise SEQ ID NO:1 or a fragment thereof having at least 5 nucleotides.

The invention relates to a recombinant expression vector comprising the nucleic acid molecule that has a nucleotide sequence that comprises SEQ ID NO:1.

The invention relates to a host cell comprising a recombinant expression vector comprising the nucleic acid molecule that has a nucleotide sequence that comprises SEQ ID NO:1.

The invention relates to an oligonucleotide molecule comprising a nucleotide sequence complementary to a nucleotide sequence of at least 5 nucleotides of SEQ ID NO:1.

The invention relates to isolated antibodies that bind to an epitope on SEQ ID NO:2.

The invention relates to methods of inhibiting expression of Dr-nm23 by contacting cells that express Dr-nm23 with a nucleic acid molecule that comprises an antisense nucleotide sequence that prevents transcription of Dr-nm23 gene sequences or translation of Dr-nm23 mRNA.

The invention relates to methods of inhibiting Dr-nm23 activity by contacting cells that express Dr-nm23 with anti-Dr-nm23 antibodies.

The invention relates to methods for prognostic determination of disease development in individuals who are suffering from CML comprising the step of determining the level of increase in expression of Dr-nm23 in "CML" cells.

The invention relates to methods for diagnosing entry into the blast crisis phase of CML in individuals who are suffering from CML comprising the step of determining the level of expression of Dr-nm23 in "CML" cells.

DETAILED DESCRIPTION OF THE INVENTION

By differential screening of a CML-blast crisis cDNA library, a novel gene with sequence homology to nm23-H1 and -H2 has been isolated. The encoded protein has -65% amino acid homology to Nm23 H1 and H2: a putative leucine zipper domain and the RGD domain implicated in integrin recognition in proteins involved in cell attachment are conserved among the different proteins.

The kinetics of DR-nm23 mRNA expression during myeloid differentiation of CD34+ cells supports a role for this gene during early stages of hematopoietic differentiation and is consistent with its identification by differential screening of a CML-blast crisis cDNA library. In this regard, comparison of DR-nm23 levels in chronic phase and blast crisis samples consistently revealed higher expression levels in the blast crisis group. DR-nm23 constitutive expression in 32Dc13 cells prevented G-CSF-induced granulocyte differentiation and caused apoptosis of these cells. The DR-nm23-transfected 32Dc13 cells require IL-3 for their growth, manifest a block in differentiation upon IL-3 removal and addition of G-CSF, and rapidly undergo cell death. This phenotype is distinct from that induced by constitutive expression of v-abl or $p210^{bcr/abl}$, which, instead, involves both IL-3-independence and inability to differentiate in response to G-CSF. As differentiation arrest is a feature of CML-blast crisis, the phenotype of DR- nm23-transfected 32Dc13 cells might be relevant to explain the alteration of the hematopoietic differentiation program typical of that disease stage. In contrast, in chronic phase, CML progenitor cells retain the ability to differentiate despite the expression of the BCR-ABL protein; this is consistent with the limited leukemogenic potential of BCR-ABL proteins, as reflected by in vitro and in vivo studies.

It is now known that BCR-ABL expression prolongs the survival of CML myeloid cells by inhibiting apoptosis. Coexpression of BCR-ABL and of a gene like DR-nm23 might generate a cell phenotype resembling that of CML-blast crisis marrow progenitor cells.

The new gene that has been discovered, Dr-nm23, is overexpressed in CML cells that are in blast crisis stage. The discovery of Dr-nm23 provides the means to determine the development of CML from chronic stage to blast crisis stage. In addition, the protein encoded by the Dr-nm23 gene can be used to study its role in CML and other diseases and conditions and to design and discover specific inhibitors, activators and other related compositions of Dr-nm23. According to the present invention, detection of Dr-nm23 mRNA or protein may be used to track development of CML. Overexpressed levels of DR-nm23 indicate that the patient is about to enter blast crisis. Samples of CML cells may be obtained at different times from individuals diagnosed with CML screen and the relative level of expression of DR-nm23 indicates the progress of the disease. The invention may be used to diagnose entry into the blast crisis phase of CML in patients who have been identified as having CML. The present invention relates to reagents useful in assays to determine Dr-nm23 expression levels. Kits are provided for performing the diagnostic and prognostic methods using samples from patients with CML.

A nucleotide sequence that encodes DR-nm23 is disclosed herein as SEQ ID NO:1, and allows for the production of pure protein, the design of probes which specifically hybridize to nucleic acid molecules that encode the Dr-nm23 and antisense compounds to inhibit transcription of Dr-nm23. Anti-Dr-nm23 antibodies are provided. Anti-Dr-nm23 antibodies may be used as reagents to detect the presence of Dr-nm23, as inhibitors of Dr-nm23 and may be used in methods of detecting the presence and/or quantity of Dr-nm23 in a sample, methods of isolating pure Dr-nm23 and methods of inhibiting Dr-nm23 activity.

The present invention provides substantially purified Dr-nm23 which has the amino acid sequence set forth in SEQ ID NO:2. Dr-nm23 can be isolated from natural sources, produced by recombinant DNA methods or synthesized by standard protein synthesis techniques.

Antibodies which specifically bind to Dr-nm23 may be used to purify the protein from natural sources using well known techniques and readily available starting materials. Such antibodies may also be used to purify the Dr-nm23 from material present when producing the protein by recombinant DNA methodology. The present invention relates to antibodies that bind to an epitope which is present on SEQ ID NO:2. As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies.

Antibodies that bind to an epitope which is present on an Dr-nm23 are useful to isolate and purify DR-nm23 from both natural sources or recombinant expression systems using well known techniques such as affinity chromatography. Such antibodies are useful to detect the presence and/or quantity of such protein in a sample and to determine if cells are expressing the protein and at what level of expression.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, the Dr-nm23 protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to Dr-nm23, the hybridoma which produces them is cultured to produce a continuous supply of antibodies.

Using standard techniques and readily available starting materials, a nucleic acid molecule that encodes Dr-nm23 may be isolated from a cDNA library, using probes or primers which are designed using the nucleotide sequence information disclosed in SEQ ID NO:1. The present invention relates to an isolated nucleic acid molecule that comprises a nucleotide sequence that encodes Dr-nm23 that comprises the amino acid sequence of SEQ ID NO:2. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing Dr-nm23.

A cDNA library may be generated by well known techniques. A cDNA clone which contains one of the nucleotide sequences set out is identified using probes that comprise at least a portion of the nucleotide sequence disclosed in SEQ ID NO:1. The probes have at least 16 nucleotides, preferably 24 nucleotides. The probes are used to screen the cDNA library using standard hybridization techniques. Alternatively, genomic clones may be isolated using genomic DNA from any human cell as a starting material. The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides. Isolated nucleic acid molecules that comprise or consist of a nucleotide sequence identical or complementary to a fragment of SEQ ID NO:1 which is at least 10 nucleotides are useful as probes for identifying genes and cDNA sequence having SEQ ID NO:1, PCR primers for amplifying genes and cDNA having SEQ ID NO:1, and antisense molecules for inhibiting transcription and translation of genes and cDNA which encode Dr-nm23 having the amino acid sequence of SEQ ID NO:2.

The cDNA that encodes Dr-nm23 may be used as a molecular marker in electrophoresis assays in which cDNA from a sample is separated on an electrophoresis gel and Dr-nm23 probes are used to identify bands which hybridize to such probes. Specifically, SEQ ID NO:1 or portions thereof, may be used as a molecular marker in electrophoresis assays in which cDNA from a sample is separated on an electrophoresis gel and Dr-nm23 specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes Dr-nm23. Electrophoresis gels useful in such an assay include standard polyacrylamide gels as described in Sambrook et al., *Molecular Cloning a Laboratory Manual*, Second Ed. Cold Spring Harbor Press (1989) which is incorporated herein by reference.

The nucleotide sequence in SEQ ID NO:1 may be used to design probes, primers and complementary molecules which specifically hybridize to the unique nucleotide sequences of Dr-nm23. Probes, primers and complementary molecules which specifically hybridize to nucleotide sequence that encodes Dr-nm23 may be designed routinely by those having ordinary skill in the art.

The present invention also includes labelled oligonucleotides which are useful as probes for performing oligonucleotide hybridization methods to identify Dr-nm23. Accordingly, the present invention includes probes that can be labelled and hybridized to unique nucleotide sequences of Dr-nm23. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of Dr-nm23.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encode Dr-nm23 and insert it into an expression vector using standard techniques and readily available starting materials.

The present invention relates to a recombinant expression vector that comprises a nucleotide sequence that encodes Dr-nm23 that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes the Dr-nm23. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts to prepare recombinant expression systems for preparing the Dr-nm23.

The present invention relates to a host cell that comprises the recombinant expression vector that includes a nucleotide sequence that encodes Dr-nm23 that comprises SEQ ID NO:1. In some embodiments, the host cell comprises a recombinant expression vector that comprises SEQ ID NO:1. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes Dr-nm23 that comprises the amino acid sequence of SEQ ID NO:2. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes Dr-nm23 is operably linked to a mammary cell specific promoter whereby the coding sequence is only expressed in mammary cells and the recombinant protein so expressed is recovered from the animal's milk. In some embodiments, the coding sequence that encodes Dr-nm23 is SEQ ID NO:1.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce Dr-nm23 using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes Dr-nm23 is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate Dr-nm23 that is produced using such expression systems. The methods of purifying Dr-nm23 isoforms from natural sources using antibodies which specifically bind to Dr-nm23 as described above, may be equally applied to purifying Dr-nm23 produced by recombinant DNA methodology.

Examples of genetic constructs include the Dr-nm23 coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes Dr-nm23 from readily available starting materials. Such gene constructs are useful for the production of Dr-nm23.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce Dr-nm23. Preferred animals are rodents, particularly goats, rats and mice.

In addition to producing these proteins by recombinant techniques, automated peptide synthesizers may also be employed to produce Dr-nm23. Such techniques are well known to those having ordinary skill in the art and are useful if derivatives which have substitutions not provided for in DNA-encoded protein production.

According to another aspect of the invention, transgenic animals, particularly transgenic mice, are generated. In some embodiments, the transgenic animals according to the invention contain a nucleic acid molecule which encodes Dr-nm23. Such transgenic mice may be used as animal models for studying overexpression of Dr-nm23 and for use in drug evaluation and discovery efforts to find compounds effective to inhibit or modulate the activity of Dr-nm23. One having ordinary skill in the art using standard techniques, such as those taught in U.S. Pat. No. 4,873,191 issued Oct. 10, 1989 Wagner and U.S. Pat. No. 4,736,866 issued Apr. 12, 1988 to Leder, both of which are incorporated herein by reference, can produce transgenic animals which produce the Dr-nm23 and use the animals in drug evaluation and discovery projects.

Another aspect of the present invention relates to knock-out mice and methods of using the same. In particular, transgenic mice may be generated which are homozygous for a mutated, non-functional Dr-nm23 gene which is introduced into them using well known techniques. The mice produce no functional Dr-nm23 and are useful to study the function of Dr-nm23. Furthermore, the mice may be used in assays to study the effect of test compounds on Dr-nm23 deficiency. The Dr-nm23 deficient mice can be used to determine if, how and to what extent Dr-nm23 inhibitors will effect the animal and thereby address concerns associated with inhibiting the activity of the molecule.

Methods of generating genetically deficient "knock out" mice are well known and disclosed in Capecchi, M. R. (1989) *Science* 244:1288–1292 and Li, P. et al. (1995) *CELL* 80:401–411, which are each incorporated herein by reference. The human Dr-nm23 cDNA clone can be used to isolate a murine Dr-nm23 genomic clone. The genomic clone can be used to prepare a Dr-nm23 targeting construct which can disrupt the Dr-nm23 gene in the mouse by homologous recombination.

The targeting construct contains a non-functioning portion of the Dr-nm23 gene which inserts in place of the functioning portion of the native mouse gene. The nonfunctioning insert generally contains an insertion in the exon that encodes the active region of Dr-nm23. The targeting construct can contain markers for both positive and negative selection. The positive selection marker allows for the selective elimination of cells without it while the negative selection marker allows for the elimination of cells that carry it.

For example, a first selectable marker is a positive marker that will allow for the survival of cells carrying it. In some embodiments, the first selectable marker is an antibiotic resistance gene such as the neomycin resistance gene can be placed within the coding sequences of the Dr-nm23 gene to render it non-functional while additionally rendering the construct selectable. The antibiotic resistance gene is within the homologous region which can recombine with native sequences. Thus, upon homologous reconstruction, the non-functional and antibiotic resistance selectable gene sequences will be taken up.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Clones are then injected into the blastocysts and implanted into pseudopregnant females. Chimeric offspring which are capable of transferring the recombinant genes in their germline are selected, mated and their offspring is examined for heterozygous carriers of the recombined genes. Mating of the heterozygous offspring can then be used to generate fully homozygous offspring which are the Dr-nm23-deficient knock out mouse.

The present invention relates to methods of and compositions for inhibiting the expression of Dr-nm23 in cells. In one embodiment, antisense oligonucleotides are provided which have a nucleotide sequence complementary to a nucleotide sequence of mRNA that encodes Dr-nm23.

The antisense oligonucleotides of the present invention comprise sequences complementary to regions of Dr-nm23 mRNA. The oligonucleotides comprise a sequence complementary to a region selected from the sequence of Dr-nm23 mRNA. The antisense oligonucleotides include single stranded DNA sequence and an antisense RNA oligonucleotide produced from an expression vector. Each of the antisense oligonucleotides of the present invention are complementary to regions of the Dr-nm23 mRNA sequence.

The antisense oligonucleotides of the present invention comprises a sequence complementary to a fragment of SEQ ID NO:1. See Ullrich et al., *EMBO J.*, 1986, 5:2503, which is incorporated herein by reference. Contemplated by this definition are fragments of oligos within the coding sequence for Dr-nm23. Oligonucleotides are preferably complementary to a nucleotide sequence that is 5-50 nucleotides in length, in some embodiments 8–40, more preferably 12–25 nucleotides, in some embodiments 10–15 nucleotides and in some embodiments 12–20 nucleotides.

In addition, mismatches within the sequences identified above, which achieve the methods of the invention, such that the mismatched sequences are substantially complementary to the Dr-nm23 sequences are also considered within the scope of the disclosure. Mismatches which permit substantial complementarily to the Dr-nm23 sequences will be known to those of skill in the art once armed with the present disclosure. The oligos may also be unmodified or modified.

The present invention is also directed to a method of inhibiting Dr-nm23 expression in mammals comprising contacting the mammal with an effective amount of an antisense oligonucleotide having a sequence which is complementary to a region of the Dr-nm23 mRNA.

Methods of administering the antisense oligos of the present invention include techniques well known in the art such as and not limited to liposomes, plasmid expression, or viral vector including retroviral vectors. In the administration of oligos via vectors or plasmids, a non-coding RNA strand of Dr-nm23 is preferably used in order to produce antisense RNA oligos which are expressed by the cell. The RNA oligos then bind Dr-nm23 sense or coding RNA sequence.

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting Dr-nm23 expression. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty μg/ml antisense oligo was used for in vitro methods of providing oligos in media for cell growth in culture. This concentration may be extrapolated for in vivo use. The concentration of antisense oligonucleotides for in vivo use is about 40 μ/g body weight. The in vivo use of the expression vector expressing RNA oligonucleotides is determined by the number of transfected cells.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.*, 1986, 859, 88–94.

The present invention provides the means and methodology for identifying CML patients entering blast crisis phase, for tracking the progress of CML disease in individuals with CML and for diagnosing blast crisis in individuals who have CML. The discovery of Dr-nm23 and that overexpression of Dr-nm23 is associated with transition from chronic phase to blast crisis phase in CML allows for the more accurate diagnostic and prognostic evaluation of the stage of CML in patent with the diseases. In particular, reagents and assays may be designed to detect and quantify Dr-nm23 expression levels. Reagents may be designed to detect Dr-nm23 protein or mRNA.

According to some embodiments, diagnostic reagents and kits are provided for performing immunoassays to determine the relative amount of Dr-nm23 protein in samples from an individual. Kits may additionally include one or more of the following: means for detecting antibodies bound to Dr-nm23 present in a sample, instructions for performing the method. In addition, kits may comprise optional positive controls such as Dr-nm23 protein. Further, optional negative controls may be provided.

Immunoassay methods may be used to determine the level of DR-nm23 expression in samples taken from CML patients at various times in order to detect increases in Dr-nm23. The antibodies are preferably monoclonal antibodies. The antibodies are preferably raised against Dr-nm23 made in human cells. Immunoassays are well known and there design may be routinely undertaken by those having ordinary skill in the art. Those having ordinary skill in the art can produce monoclonal antibodies which specifically bind to Dr-nm23 useful in methods and kits of the invention using standard techniques and readily available starting materials. The techniques for producing monoclonal antibodies are outlined in Harlow, E. and D. Lane (1988) *Antibodies: A Laboratory Manual*, Cold Spring Harbor Laboratory, Cold Spring Harbor, N.Y., which is incorporated herein by reference, provide detailed guidance for the production of hybridomas and monoclonal antibodies which specifically bind to Dr-nm23.

According to some embodiments, immunoassays comprise allowing proteins in the sample to bind a solid phase support such as a plastic surface. Detectable antibodies are then added which selectively binding to Dr-nm23. Detection of the detectable antibody indicates the presence of Dr-nm23. The detectable antibody may be a labelled or an unlabelled antibody. Unlabelled antibody may be detected using a second, labelled antibody that specifically binds to the first antibody or a second, unlabelled antibody which can be detected using labelled protein A, a protein that complexes with antibodies. Various immunoassay procedures are described in *Immunoassays for the 80's*, Voller, et al., Ed., University Park, 1981, which is incorporated herein by reference. The amount of antibodies present may be quantified by well known techniques.

Simple immunoassays may be performed in which a solid phase support is contacted with the test sample. Any proteins resent in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, (1970) Kirkham, Ed., E. & S. Livingstone, Edinburgh, pp. 199–206, which is incorporated herein by reference.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays.

The reverse assay may also be adapted in a similar manner for the detection of antibodies in a test sample.

The first component of the immunometric assay may be added to nitrocellulose or other solid phase support which is capable of immobilizing proteins. The first component for determining the presence of Dr-nm23 in a test sample is anti-Dr-nm23 antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the quantity of Dr-nm23, detectable anti-Dr-nm23 antibodies are used. Several methods are well known for the detection of antibodies. Anti-Dr-nm23 antibodies may be labelled with a radioisotope and the amount of radioisotope may be determined using a scintillation counter.

One method in which the antibodies can be detectably labelled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labelled is through radioactive isotopes and subsequent use in a radioimmunoassay (RIA) (see, for example, Work, et al., *Laboratory Techniques and Biochemistry in Molecular Biology*, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labelled antibody is exposed to light of the proper wavelength, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labelled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibodies can also be detectably labelled by coupling to a chemiluminescent compound. The presence of the chemiluminescent-labelled antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of Dr-nm23 and no Dr-nm23, respectively, are added to assays being performed in parallel with the test assay. One skilled in the art would have the necessary knowledge to perform the appropriate controls.

Dr-nm23 may be produced as a reagent for positive controls routinely. One skilled in the art would appreciate the different manners in which the Dr-nm23 may be produced and isolated.

To examine a test sample for the presence or absence of Dr-nm23, a standard immunometric assay such as the one described herein may be performed. A first anti-Dr-nm23 antibody is added to a 96-well microtiter plate in a volume of buffer. The plate is incubated for a period of time sufficient for binding to occur and subsequently washed with PBS to remove unbound antibody. The plate is then blocked with a PBS/BSA solution to prevent sample proteins from non-specifically binding the microtiter plate. Test sample are subsequently added to the wells and the plate is incubated for a period of time sufficient for binding to occur. The wells are washed with PBS to remove unbound protein. Labelled anti-Dr-nm23 antibodies, which recognize portions of Dr-nm23 not recognized by the first antibody, are added to the wells. The plate is incubated for a period of time sufficient for binding to occur and subsequently washed with PBS to remove unbound, labelled anti-Dr-nm23 antibody. The amount of labelled and bound anti-Dr-nm23 antibody is subsequently determined by standard techniques.

Kits which are useful for the detection of Dr-nm23 in a test sample comprise a container comprising anti-Dr-nm23 antibodies and a container or containers comprising controls. Controls include one control sample which does not contain Dr-nm23 and/or another control sample which contained Dr-nm23. The anti-Dr-nm23 antibodies used in the kit are detectable such as being detectably labelled. If the detectable anti-Dr-nm23 antibody is not labelled, it may be detected by second antibodies or protein A for example which may also be provided in some kits in separate containers. Additional components in some kits include solid support, buffer, and instructions for carrying out the assay. The immunoassay is useful for detecting Dr-nm23 in homogenized tissue samples and body fluid samples including the plasma portion or cells in the fluid sample.

Western blots may be used in methods of detecting the presence of Dr-nm23 in samples of tissue. Western blots use detectable anti-Dr-nm23 antibodies to bind to any Dr-nm23 present in a sample and thus indicate the presence of the protein in the sample. Western blot techniques, which are described in Sambrook, J. et al., (1989) *Molecular Cloning: A Laboratory Manual*, Cold Spring Harbor Laboratory Press, Cold Spring Harbor, N.Y., which is incorporated herein by reference, are similar to immunoassays with the essential difference being that prior to exposing the sample to the antibodies, the proteins in the samples are separated by gel electrophoresis and the separated proteins are then probed with antibodies. In some preferred embodiments, the matrix is an SDS-PAGE gel matrix and the separated proteins in the matrix are transferred to a carrier such as filter paper prior to probing with antibodies. Anti-Dr-nm23 antibodies described above are useful in Western blot methods.

Generally, samples are homogenized and cells are lysed using detergent such as Triton-X. The material is then separated by the standard techniques in Sambrook, J. et al., (1989) *Molecular Cloning: A Laboratory Manual*, Cold Spring Harbor Laboratory Press, Cold Spring Harbor, N.Y.

Kits which are useful for the detection of Dr-nm23 in a test sample by Western blot comprise a container comprising Dr-nm23 antibodies and a container or containers comprising controls. Controls include one control sample which does not contain Dr-nm23 and/or another control sample which contained Dr-nm23. The anti-Dr-nm23 antibodies used in the kit are detectable such as being detectably labelled. If the detectable anti-Dr-nm23 is not labelled, it may be detected by second antibodies or protein A for example which may also be provided in some kits in separate containers. Additional components in some kits include instructions for carrying out the assay.

Aspects of the present invention also include various methods of determining the level of expression of Dr-nm23 by sequence-based molecular analysis. Several different methods are available for doing so including those using Polymerase Chain Reaction (PCR) technology, using Northern blot technology, oligonucleotide hybridization technology, and in situ hybridization technology. According to the invention, samples are screened to determine the level of expression of Dr-nm23.

The invention relates to probes and primers used in the methods of identifying the presence and quantity of mRNA that encodes Dr-nm23 and to diagnostic kits which comprise such components. The mRNA sequence-based methods for determining whether a sample mRNA encoding Dr-nm23 include but are not limited to PCR technology, Northern and Southern blot technology, in situ hybridization technology and oligonucleotide hybridization technology.

The methods described herein are meant to exemplify how the present invention may be practiced and are not meant to limit the scope of invention. It is contemplated that other sequence-based methodology for detecting the presence and quantity of specific mRNA that encodes Dr-nm23 in tissue samples may be employed according to the invention.

PCR primers can be designed routinely by those having ordinary skill in the art using well known cDNA sequence information. Primers are generally 8–50 nucleotides, preferably 18–28 nucleotides. A set of primers contains two primers. PCR product, i.e. amplified DNA, may be detected by several well known means. The preferred method for detecting the presence of amplified DNA is to separate the PCR reaction material by gel electrophoresis and stain the gel with ethidium bromide in order to visual the amplified DNA if present. A size standard of the expected size of the amplified DNA is preferably run on the gel as a control.

The present invention includes oligonucleotide which are useful as primers for performing PCR methods to amplify mRNA or cDNA that encodes Dr-nm23 protein. According to the invention, diagnostic kits can be assembled which are useful to practice methods of detecting the presence of mRNA or cDNA that encodes Dr-nm23 in tissue samples. Such diagnostic kits comprise oligonucleotide which are useful as primers for performing PCR methods. It is preferred that diagnostic kits according to the present invention comprise a container comprising a size marker to be run as a standard on a gel used to detect the presence of amplified DNA. The size marker is the same size as the DNA generated by the primers in the presence of the mRNA or cDNA encoding Dr-nm23.

Another method of determining whether a sample contains cells expressing Dr-nm23 is by Northern blot analysis of mRNA extracted from a tissue sample. The techniques for performing Northern blot analyses are well known by those having ordinary skill in the art and are described in Sambrook, J. et al., *Molecular Cloning: A Laboratory Manual*, (1989) Cold Spring Harbor Laboratory Press, Cold Spring Harbor, N.Y. mRNA extraction, electrophoretic separation of the mRNA, blotting, probe preparation and hybridization are all well known techniques that can be routinely performed using readily available starting material.

One having ordinary skill in the art, performing routine techniques, could design probes to identify mRNA encoding Dr-nm23 using the information in SEQ ID NO:1. The mRNA is extracted using poly dT columns and the material is separated by electrophoresis and, for example, transferred to nitrocellulose paper. Labelled probes made from an isolated specific fragment or fragments can be used to visualize the presence of a complementary fragment fixed to the paper.

According to the invention, diagnostic kits can be assembled which are useful to practice methods of detecting the presence of mRNA that encodes Dr-nm23 in tissue samples by Northern blot analysis. Such diagnostic kits comprise oligonucleotide which are useful as probes for hybridizing to the mRNA. The probes may be radiolabelled.

It is preferred that diagnostic kits according to the present invention comprise a container comprising a size marker to be run as a standard on a gel. It is preferred that diagnostic kits according to the present invention comprise a container comprising a positive control which will hybridize to the probe.

Another method of detecting the presence of mRNA encoding Dr-nm23 protein is by oligonucleotide hybridization technology. Oligonucleotide hybridization technology is well known to those having ordinary skill in the art. Briefly, detectable probes which contain a specific nucleotide sequence that will hybridize to nucleotide sequence of mRNA encoding Dr-nm23 protein. RNA or cDNA made from RNA from a sample is fixed, usually to filter paper or the like. The probes are added and maintained under conditions that permit hybridization only if the probes fully complement the fixed genetic material. The conditions are sufficiently stringent to wash off probes in which only a portion of the probe hybridizes to the fixed material. Detection of the probe on the washed filter indicate complementary sequences. One having ordinary skill in the art, using the sequence information disclosed in SEQ ID NO:1 can design probes which are fully complementary to mRNA sequences but not genomic DNA sequences. Hybridization conditions can be routinely optimized to minimize background signal by non-fully complementary hybridization.

The present invention includes labelled oligonucleotide which are useful as probes for performing oligonucleotide hybridization. That is, they are fully complementary with mRNA sequences but not genomic sequences. For example, the mRNA sequence includes portions encoded by different exons. The labelled probes of the present invention are labelled with radiolabelled nucleotides or are otherwise detectable by readily available nonradioactive detection systems. Labelled probes allow for the Dr-nm23 mRNA to be quantified.

According to the invention, diagnostic kits can be assembled which are useful to practice oligonucleotide hybridization methods of the invention. Such diagnostic kits comprise a labelled oligonucleotide which encodes portions of Dr-nm23 encoded by different exons. It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

The present invention relates to in vitro kits for evaluating tissues samples to determine the level of Dr-nm23 expression and to reagents and compositions useful to practice the same.

In situ hybridization technology is well known by those having ordinary skill in the art. Briefly, cells are fixed and detectable probes which contain a specific nucleotide sequence are added to the fixed cells. If the cells contain complementary nucleotide sequences, the probes, which can be detected, will hybridize to them. One having ordinary skill in the art, using the sequence information in SEQ ID NO:1 can design probes useful in in situ hybridization technology to identify cells that express Dr-nm23.

The probes are fully complementary and do not hybridize well to partially complementary sequences. For in situ hybridization according to the invention, it is preferred that the probes are detectable by fluorescence. A common procedure is to label probe with biotin-modified nucleotide and then detect with fluorescently-tagged avidin. Hence, probe does not itself have to be labelled with florescent but can be subsequently detected with florescent marker.

Cells are fixed and the probes are added to the genetic material. Probes will hybridize to the complementary nucleic acid sequences present in the sample. Using a fluorescent microscope, the probes can be visualized by their fluorescent markers.

According to the invention, diagnostic kits can be assembled which are useful to practice in situ hybridization methods of the invention are fully complementary with mRNA sequences but not genomic sequences. For example, the mRNA sequence includes portions encoded by different exons. It is preferred that labelled probes of the in situ diagnostic kits according to the present invention are labelled with a fluorescent marker.

Immunohistochemistry techniques may be used to identify and essentially stain cells with Dr-nm23. Anti-Dr-nm23 antibodies, such as those described above, are contacted with fixed cells and the Dr-nm23 present in the cells reacts with the antibodies. The antibodies are detectably labelled or detected using labelled second antibody or protein A to stain the cells.

EXAMPLE

Materials and Methods Screening of a CML-blast crisis cDNA Library

A CML-blast crisis cDNA library was prepared in the pcDNA1 vector, based on a modified method of Gubler and Hoffman (Gubler, V. and Hoffman, B. J. Gene 25:263–269, 1983) and manufacturers specifications (Invitrogen, Corp.). 5µof poly (A)+RNA were used for first-strand cDNA synthesis employing an oligo(dT) primer that incorporated the NotI restriction site, and Moloney murine leukemia reverse transcriptase. Following second-strand synthesis utilizing RNAse H and DNA polymerase, cDNA was blunt-ended with $T_4$ DNA polymerase. The cDNAs were size-fractionated on Sephacryl S-400 spin columns (Promega) which separated cDNAs smaller than 271 bp. After ethanol precipitation, BstXI-EcoRI regenerative non-palindromic adaptors (5'GAATTCCACCACA3'- SEQ ID NO:3; 3'CTTAAGGTG5'—SEQ ID NO:4) were ligated to the double stranded cDNA via $T_4$ DNA ligase. The cDNA was digested with BstXI-NotI and ligated to the BstXI-NotI predigested pcDNA1 vector. 20 µl of ligation stock were used to transform competent MC1061/P3 bacteria and $10^6$ primary clones were obtained. The library was amplified once prior to screening.

For screening, $2 \times 10^5$ colonies of the CML-blast crisis cDNA library were plated and screened by differential hybridization of replicate filters. Filters were prehybridized for at least 4 h at 42° C. in 5× SSC, 50% formamide. Hybridization was performed in 5× SSC, 50% formamide, 5× Denhardt's solution, 100 µg/ml salmon sperm DNA, and $^{32}$P-labelled cDNA probes ($2 \times 10^6$/ml) generated by reverse transcription of poly(A)+ RNA from either the CCRF-CEM cell line or CML-blast crisis primary cells.

Final washes of the filters were for 1 h in 1× SSC, 0.1% SDS, at 65° C. Clones differentially hybridizing were subjected to two additional rounds of differential screening. One clone called clone 126 was identified and was found to be of interest.

DNA Sequencing

Double-stranded DNA sequencing of plasmid DNA was performed utilizing Sequenase (US Biochemicals) and synthetic oligonucleotide primers via the dideoxy chain termination method.

RNA Preparation and Northern Blot Analysis

Cells were rinsed with phosphate-buffered saline (PBS) and resuspended in guanidium isothiocyanate followed by centrifugation over cesium chloride. Total RNA (20 $\mu$g) was fractionated by electrophoresis in 1.2% agarose gels containing 0.66M formaldehyde and MOPS buffer (40 mM morpholinopropanesulfonic acid, 10 mM sodium acetate, 10 mM EDTA [pH 7.2]) and blotted onto Zetabind membrane (Schleicher and Schuell). Clone 126 insert or the full-length cDNA was used as probe after random primer labeling with $\alpha$-[32P]dCTP.

Cloning of the full-length DR-nm23

DR-nm23 was identified as a sequence (clone 126) differentially expressed in CML-BC cells relative to CCRF-CEM cells. This clone contained an insert of 652 bp that lacked the initiation codon and was shorter of the corresponding RNA transcripts detected by Northern blot hybridization.

The full-length cDNA was cloned in four successive steps: i) a K562 cDNA library in $\lambda$gt10 was screened to identify additional DR-nm23 clones; ii) after identification of several positive clones, the longest EcoRl insert (820 bp) was subcloned into the EcoR1 site of an SK plasmid vector (Stratagene), and named pDR-12. Sequence analysis revealed that it was still lacking the region around the initiation codon; iii) to reconstitute the remaining 5' segment, a human placental genomic library in $\lambda$FIX II (Clontec) was screened with a $^{32}$P-labeled insert of DR-nm23. Clone 1 contained the entire coding region of DR-nm23 within a BamHI/Notl 1450 bp fragment; iii) clone DR-12 was digested with EcoRl to release the 820 bp insert . This insert was then digested with Mbo II and an 804 bp fragment was isolated. The genomic BamHI-Notl insert from clone 1 was digested with Mbo 11 and a 45 bp fragment was isolated. This was then ligated via a triple component ligation with the 804 bp fragment into BamH1 and EcoRl-digested SK vector. The resulting clones, designated DR-9 and DR-11, were sequenced and shown to contain the full-length cDNA with an ATG and an in-frame TAG stop codon.

Cloning of LXSN-DR-nm23

For cloning into mammalian expression vectors, the majority of the 3' untranslated region of the full-length DR-m23 cDNA was removed by Rsal digestion. The resulting 698 bp fragment was blunt-ended and ligated to plasmid LXSN, digested with Xhol, and then blunt-ended with Klenow enzyme. The resulting plasmid, designated LXSN-DR-nm23, confers also resistance to the antibiotic G418.

Cloning of hemagglutinin (HA) -tagged DR-nm23

The full-length DR-nm23 cDNA was excised by BamHI-EcoRl digestion of the pSK plasmid and then digested with BsrI, generating two fragments (499 and 365 nucleotides, respectively), the longer of which contained most of DR-nm23 coding region. Primers (F 5'TGTATGAGCAGG3'—SEQ ID NO:5 and G 5'-AATTCCTGCTCATACAGC-3' SEQ ID NO:6) not including the TAG stop codon, replaced by CAG, were annealed to yield a double-stranded DNA oligomer flanked by BsrI and EcoRl overhangs. Recombinant DR-nm23 devoid of the TAG codon was generated by ligation of the annealed primers with the 499 bp fragment into a BamHI-EcoRl digested pSK plasmid. This plasmid was designated pSKDRlmutC. From plasmid SKA-myb 5' HA3, the hemagglutinin (HA) triple epitope was excised via Xhol-Sall digestion and subcloned at the Xhol site of pSKDR-nm23mutC. To maintain the construct in frame, an extra nucleotide was inserted by polymerase chain reaction (PCR). A 5' primer (5'GTCGACCTCGAGGCCACCATGG3' SEQ ID NO:7) and the T7 primer were used on the template plasmid pSKDR-nm23mutC to generate a 163 bp product. This was cleaved with Xhol-Kpnl and subcloned into Xhol-Kpnl-digested pSKDR-nm23mutC. The reading frame was verified by sequencing. This construct was called pSKDR-nm23HA3.

Cell culture and primary cells

The murine IL-3 dependent myeloid cell line 32Dc13 was used. For proliferation studies, 5×10$^4$ cells/ml were plated in 4 ml of Iscove's Modified Dulbecco Medium (IMDM) supplemented with 10% heat-inactivated fetal bovine serum (FBS), 15% WEHI (IL-3 producer) conditioned medium, 100 U/ml penicillin-streptomycin and 200 $\mu$g/ml L-glutamine. Growth was monitored counting viable cells at daily intervals. For differentiation studies, 2.5×10$^5$ cells/ml were plated in 4 ml IMDM supplemented with 10% conditioned medium from the U87MG (G-CSF producer) cell line. Human hematopoietic progenitor cells were purified from the peripheral blood of healthy donors by a four-step procedure and cultured (10$^4$ cells/ml) in IMDM supplemented with bovine serum albumin (10 mg/ml), human transferrin (1 mg/ml), human low density lipoprotein (40 $\mu$g/ml), insulin (10 $\mu$g/ml), sodium pyruvate (0.1 $\mu$M), L-glutamine (2 mM), ferrous sulfate (40 mM), nucleosides (each at 10 $\mu$g/ml), human recombinant IL-3 (100 U/ml) and GM-CSF (20 ng/ml). Cultures were incubated in a humified 5% CO$_2$ atmosphere at 37° C.

RT-PCR detection of DR-mm23 and myeloperoxidase mRNAs in CD34+ and in 32Dc13 cells RNA was extracted from cultured CD34+ and 32Dc13 cells. The first-strand cDNA reaction was performed using 10% of the extracted RNA (10–30 ng), 200 U of Moloney murine leukemia virus reverse transcriptase (M-MLV Reverse Transcriptase, GIBCO-BRL), 200 $\mu$M of each deoxynucleoside triphosphate (dNTP), 15 U RNAsin (Promega) 5×10$^3$ U random hexamer (Pharmacia) in a 20 $\mu$l reaction containing 10 mM DTT; 50 mM Tris pH8.3, 75 mM KCL and 3 mM MgCI$_2$. The reverse transcriptase (RT) reaction was carried out at 37° C. for 90 min. To analyze DR-nm23 mRNA expression, PCR amplification was performed on 20% of the first-strand reaction product denatured at 100° C. for 5 min, 300 ng of the 5' and 3' primers (5'GCA CCTTCCTGGCCGTGAAG3' SEQ ID NO:8, and 5'AGGT-GCGCACCACGTCCAG3' SEQ ID NO:9, respectively), 200 mM of each deoxynucleoside 30 triphosphate (dNTP), 1× Taq polymerase buffer supplemented with Mg++ (Boehringer Mannheim) and 0.5 U of Taq polymerase (Boehringer Mannheim) in a reaction volume of 50 $\mu$l. PCR reactions (25 cycles) were carried out in a Perkin Elmer Cetus thermocycler (30 s at 94° C., 45 s at 55° C., and 45 s at 72° C.). Amplified DNA was electrophoresed on a 2.5% seakem agarose gel (FMC Byoproducts), transferred onto Hybond-N nylon membrane (Amersham), fixed with UV Stratalinker (Stratagene) and detected by Southern hybridization with a [$^{32}$P] $\gamma$-ATP end-labeled oligoprobe (5'TAGTGCTCACGCAGCAGCT3' SEQ ID NO:10) specific for the amplified sequence. For studies of myeloperoxidase mRNA expression, PCR amplification with myeloperoxidase (MPO) specific primers, and Southern blot detection with a specific probe.

Transfection of 32Dcl3 cells

32D C13 cells (5×10⁶) were resuspended in 0.5 ml PBS and electroporated (Gene Pulser Biorad; 340V/250 μF) with 15 μg of plasmid DNA. Cells were then resuspended in 12.5 ml IMDM supplemented with 10% heat-inactivated FBS, 15% WEHI conditioned medium, 100 units/ml penicillin-streptomycin and 200 μg/ml L-glutamine. Cells were washed 48 h later and replated in selective medium containing 1 mg/ml G418. After a 2-week selection, mixed cell populations from different transfections were expanded for further analysis.

Detection of apoptosis by DNA gel electrophoresis

Cells treated with G-CSF for 72 h were collected by centrifugation and fixed in 70% ethanol. DNA extraction and gel electrophoresis for detection of fragmented DNA was performed as described in Gong, J., Traganos, F., and Darzynkiewiez, Z. Anal. Bioch. 218:314–319, 1994.

Western Blotting

Equal numbers of cells were washed three times with ice-cold PBS prior to lysis with 1 ml lysis buffer (10 mM HEPES, pH 7.5, 150 mM NaCl, 0.5% NP-40, 10% glycerol, 10 μg/ml leupeptin, 25 μg/ml aprotinin, 1 mM PMSF and 1 mM EDTA). Lysates were incubated on ice for 30 min and centrifuged at 16,000×g for 15 min at 4° C. After three washes with lysing buffer, loading buffer (50 μl) was added and, after boiling for 5 min, samples were fractionated on a 12.5% SDS-PAGE and electrophoretically transferred to nitrocellulose membranes (Schleicher & Schuell) according to standard procedures. The membranes were blocked for 2 h in PBS containing 5% non-fat dry milk and incubated with primary antibody diluted into 1% dry milk in PBS. After several washes in PBS containing 0.1% NP-40 and 0.1% Tween-20, membranes were incubated for 2 h with sheep anti-mouse IgG conjugated to horseradish peroxidase (Amersham). Membranes were then washed and processed for detection of bound proteins using chemiluminescent substrates according to manufacturer's instructions (enhanced chemiluminescence mixture; Amersham).

Results

Cloning of the full-length DR-nm23 cDNA

Differential screening of a CML-BC cDNA library using as probe ³²P-labeled cDNA prepared from RNA of the lymphoblastic leukemia T cell line CCRF-CEM led to the identification of several clones preferentially expressed in CML-BC cells. Sequence analysis of one such clone revealed approximately a 70% homology to the mRNA sequence of the nm23 H1- and H2-genes, postulated to act as metastatic suppressor genes. This clone was named DR-nm23. The originally identified clone was only 652 bp-long, did not contain an ATG codon in the context of the canonical consensus sequence for translation initiation, and hybridized to 0.8–1.0 kb mRNA species. Thus, primer extension analysis performed on RNA derived from CML-BC and CCRF-CEM cells revealed two extension products in the RNA of expressor cells, in agreement with the existence of two mRNA transcripts of 0.8–1.0 kb. The full length DR-nm23 cDNA, obtained as described in Materials and Methods, is 849 nucleotides long and contains an open reading frame for a predicted protein of 168 amino acids. The nucleotide sequence around the first ATG was CCAT-CATGT SEQ ID NO:11, similar to the consensus sequence (CCA/GCCATGG SEQ ID NO:12) for eukaryotic mRNAs translation initiation. In agreement with the predicted amino acid sequence, in vitro translation of DR-nm23 subcloned into the transcription-translation vector pcDNA3 generated a protein of approximately 18,000 daltons.

Amino acid sequence comparison between DR-nm23 and Nm23-H1 and -H2

The DR-nm23 protein has 66.9% and 64.9% identity, respectively, to the human Nm23-H1 and -H2 proteins. The Nm23-H1 and -H2 proteins have a putative leucine zipper domain. A similar leucine zipper-like structure is present in the DR-Nm23 protein. This region spans from amino acids 60 to 84 and shares 54% and 45.8% identity to the Nm23-H1 and -H2 proteins, respectively. An RGD motif, implicated in cell attachment to fibronectin and other proteins involved in cell adhesion (19), is conserved in the Nm23 proteins: such motif, and the surrounding amino acids, is also maintained in the DR-nm23 protein. A serine residue, at position 44 in the Nm23 protein, a major phosphorylation site found to correlate with suppression of cell metastatic potential and a histidine residue at position 118 of the Nm23 protein, that is critical for its nucleoside diphosphate kinase (NDPK) activity are present in the predicted amino acid sequence of DR-nm23 at residues 61 and 134, respectively. DR-nm23 expression during myeloid differentiation in vitro To determine the pattern of DR-nm23 expression during hematopoietic differentiation, human peripheral blood CD34+ cells obtained from healthy donors, were induced, in the presence of human-specific growth factors, to differentiate toward the myeloid pathway.

At day 0 and after 3, 5, 7, 9, 12, 14, and 16 days of in vitro differentiation, cells were collected and assessed by RT-PCR for DR-nm23 expression. DR-nm23 mRNA was detectable in undifferentiated CD34+ cells, and readily increased on day 3 of differentiation; DR-nm23 mRNA levels declined thereafter and were only barely detectable by day 12. This pattern of expression is inversely correlated with proliferation of hematopoietic cells and is consistent with a function for DR-nm23 during early stages of hematopoiesis. Expression of DR-nm23 in 32Dc13 cells blocks G-CSF-induced granulocytic differentiation and causes apoptosis.

32Dc13 cells were derived from normal mouse marrow long term cultures and undergo terminal differentiation into neutrophilic granulocytes when cultured in the presence of G-CSF. 32Dc13 cells were transfected with the insert-less vector LXSN and with LXSN-DR-nm23, linked or not to an in-frame hemaglutinin (HA) epitope.

G418-resistant transfected cells were expanded and assessed for DR-nm23 expression. Northern blot analysis with a ³²P-labeled DR-nm23 cDNA insert revealed the expected transcripts of the DR-nm23 containing retrovirus vector in transfected cells. Endogeneous DR-nm23 transcripts were barely detectable only after a 5-day exposure of the blot, perhaps reflecting low expression levels in parental cells and/or sequence heterogeneity between mouse and human mRNAs. Use of anti-HA monoclonal antibody 12 CA5 allowed detection of a protein with the expected size for DR-nm23 and the in-frame triple HA-epitope.

The growth of parental, LXSN-, and DR-nm23-transfected 32Dc13 cells was indistinguishable, in the presence of IL-3; however, in medium lacking IL-3, DR-nm23 transfected cells died more rapidly of control cells.

Parental and LXSN- transfected 32Dc13 cells, when cultured in G-CSF, retained viability during the initial days of incubation in differentiation medium; like parental cells, LXSN-transfected 32Dc13 cells underwent terminal differentiation to morphologically recognizable granulocytes. In contrast, DR-nm23-transfected 32Dc13 cells lost viability at early times in differentiation culture and failed to terminally differentiate upon treatment with G-CSF.

Myeloperoxidase (MPO) expression is induced at early stages of 32Dc13 cell differentiation. MPO transcripts were detected in G-CSF-treated insert-less-transfected 32Dc13 cells after 3–4 days of culture. In contrast, these transcripts were undetectable in DR-nm23-transfected 32Dc13 cells up to 4 days of G-CSF treatment, after which no viable cells were recovered for RNA extraction. DR-nm23-transfected cells appeared to die of apoptosis as revealed by morphology, and DNA gel electrophoresis evidence of a typical DNA fragmentation pattern.

---

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 849 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 19..525

( x i ) SEQUENCE DESCRIPTION: SEQ ID NO:1:

```
CGCTCCCGCA CCGCCATC ATG ATC TGC CTG GTG CTG ACC ATC TTC GCT AAC          51
                    Met Ile Cys Leu Val Leu Thr Ile Phe Ala Asn
                     1           5                    10

CTC TTC CCC GCG GCC TGC ACC GGC GCA CAC GAA CGC ACC TTC CTG GCC          99
Leu Phe Pro Ala Ala Cys Thr Gly Ala His Glu Arg Thr Phe Leu Ala
             15              20                  25

GTG AAG CCG GAC GGC GTG CAG CGG CGG CTG GTG GGC GAG ATT GTG CGG         147
Val Lys Pro Asp Gly Val Gln Arg Arg Leu Val Gly Glu Ile Val Arg
         30              35              40

CGC TTC GAG AGG AAG GGC TTC AAG TTG GTG GCG CTG AAG CTG GTG CAG         195
Arg Phe Glu Arg Lys Gly Phe Lys Leu Val Ala Leu Lys Leu Val Gln
     45              50              55

TCC TCC GAG GAG CTG CTG CGT GAG CAC TAC GCC GAG CTG CGT GAA CGC         243
Ser Ser Glu Glu Leu Leu Arg Glu His Tyr Ala Glu Leu Arg Glu Arg
 60              65              70                      75

CCG TTC TAC GGC CGC CTT GTC AAG TAT ATG GCC TCC GGG CCG GTG GTG         291
Pro Phe Tyr Gly Arg Leu Val Lys Tyr Met Ala Ser Gly Pro Val Val
                 80              85                  90

GCC ATG GTT TGG CAG GGG CTG GAC GTG GTG CGC ACC TCG CGG GCG CTC         339
Ala Met Val Trp Gln Gly Leu Asp Val Val Arg Thr Ser Arg Ala Leu
             95              100             105

ATC GGA GCC ACG AAC CCG GCC GAC GCC CCG CCC GGC ACC ATC CGC GGG         387
Ile Gly Ala Thr Asn Pro Ala Asp Ala Pro Pro Gly Thr Ile Arg Gly
         110             115             120

GAT TTC TGC ATC GAG GTT GGC AAC CTG ATT CAC GGC AGC GAC TCG GTG         435
Asp Phe Cys Ile Glu Val Gly Asn Leu Ile His Gly Ser Asp Ser Val
     125             130             135

GAG AGT GCC CGC CGC GAG ATC GCT CTC TGG TTC CGC GCA GAC GAG CTC         483
Glu Ser Ala Arg Arg Glu Ile Ala Leu Trp Phe Arg Ala Asp Glu Leu
140             145             150                     155

CTC TGC TGG GAG GAC AGC GCT GGG CAC TGG CTG TAT GAG TAG             525
Leu Cys Trp Glu Asp Ser Ala Gly His Trp Leu Tyr Glu *
                 160             165

CCCGGCAGAT GCGCGTCACA GAGGCTCTCA CATTCCAGCC TCCTCCAGGG CCCAGGTGGG        585

CGGCTTCTGG CCCCACCCCA CAGCGCTTGG AGCATCCCTT TGGACGGGCT GCTGAACATC        645
```

```
CACCTGTCTG  GACGTTGCAT  GGAGGGTGGC  GCAGCCTCTC  CAATCCCTGG  CGTACAGGGT      705

TTCCTGCCCG  AGGACCTGCT  CCAGGAGCCT  GCGCGGCTCG  CCTGGAAACG  TGCCAGGAGC      765

ACTGTCCTGG  TGCCCAGCCC  AACGTGGTCC  AAGGTTTTTT  TATAATTAAA  GTCCTCGTTT      825

TCGTTAAAAA  AAAAAAAAAA  AAAA                                                849
```

( 2 ) INFORMATION FOR SEQ ID NO:2:

( i ) SEQUENCE CHARACTERISTICS:
        ( A ) LENGTH: 168 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ile  Cys  Leu  Val  Leu  Thr  Ile  Phe  Ala  Asn  Leu  Phe  Pro  Ala  Ala
 1              5                        10                       15

Cys  Thr  Gly  Ala  His  Glu  Arg  Thr  Phe  Leu  Ala  Val  Lys  Pro  Asp  Gly
               20                        25                       30

Val  Gln  Arg  Arg  Leu  Val  Gly  Glu  Ile  Val  Arg  Arg  Phe  Glu  Arg  Lys
          35                        40                       45

Gly  Phe  Lys  Leu  Val  Ala  Leu  Lys  Leu  Val  Gln  Ser  Ser  Glu  Glu  Leu
     50                        55                       60

Leu  Arg  Glu  His  Tyr  Ala  Glu  Leu  Arg  Glu  Arg  Pro  Phe  Tyr  Gly  Arg
65                        70                       75                       80

Leu  Val  Lys  Tyr  Met  Ala  Ser  Gly  Pro  Val  Ala  Met  Val  Trp  Gln
                    85                        90                       95

Gly  Leu  Asp  Val  Val  Arg  Thr  Ser  Arg  Ala  Leu  Ile  Gly  Ala  Thr  Asn
               100                       105                      110

Pro  Ala  Asp  Ala  Pro  Pro  Gly  Thr  Ile  Arg  Gly  Asp  Phe  Cys  Ile  Glu
          115                       120                      125

Val  Gly  Asn  Leu  Ile  His  Gly  Ser  Asp  Ser  Val  Glu  Ser  Ala  Arg  Arg
     130                       135                      140

Glu  Ile  Ala  Leu  Trp  Phe  Arg  Ala  Asp  Glu  Leu  Leu  Cys  Trp  Glu  Asp
145                       150                      155                      160

Ser  Ala  Gly  His  Trp  Leu  Tyr  Glu
                    165
```

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GAATTCCACC  ACA                                                              13
```

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GTGGAATTC                                                                                                           9

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TGTATGAGCA GG                                                                                                      12

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AATTCCTGCT CATACAGC                                                                                                18

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GTCGACCTCG AGGCCACCAT GG                                                                                           22

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCACCTTCCT GGCCGTGAAG                                                                                              20

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGGTGCGCAC CACGTCCAG                                                                                               19

( 2 ) INFORMATION FOR SEQ ID NO:10:

(  i  ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:10:

TAGTGCTCAC GCAGCAGCT                                                                                    19

( 2 ) INFORMATION FOR SEQ ID NO:11:

(  i  ) SEQUENCE CHARACTERISTICS:
                ( A ) LENGTH: 9 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:11:

CCATCATGT                                                                                                9

( 2 ) INFORMATION FOR SEQ ID NO:12:

(  i  ) SEQUENCE CHARACTERISTICS:
                ( A ) LENGTH: 9 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:12:

CCRCCATGG                                                                                                9

We claim:

1. An isolated nucleic acid molecule that comprises a nucleic acid sequence that encodes a protein having the amino acid sequence of SEQ ID NO:2.

2. A pharmaceutical composition comprising the nucleic acid molecule of claim 1 and a pharmaceutically acceptable carrier.

3. An isolated nucleic acid molecule consisting of SEQ ID NO: 1 wherein said nucleic acid molecule encodes a protein which is an indicator of entry into blast crisis or a fragment of the coding sequence of SEQ ID NO: 1 having at least 10 nucleotides.

4. The nucleic acid molecule of claim 3 consisting of SEQ ID NO:1.

5. A recombinant expression vector comprising the nucleic acid molecule of claim 4.

6. A host cell comprising the recombinant expression vector of claim 5.

7. The nucleic acid molecule of claim 3 consisting of a fragment of the coding sequence of SEQ ID NO: 1 having at least 10 nucleotides.

8. The nucleic acid molecule of claim 3 consisting of a fragment of the coding sequence of SEQ ID NO: 1 having 12–150 nucleotides.

9. The nucleic acid molecule of claim 3 consisting of a fragment of the coding sequence of SEQ ID NO: 1 having 15–50 nucleotides.

10. An oligonucleotide molecule consisting of between 10 and 100 nucleotides comprising a nucleotide sequence complementary to a nucleotide sequence of at least 5 nucleotides of SEQ ID NO:1 wherein SEQ ID NO:1 encodes a protein which is an indicator of entry into blast crisis.

11. The oligonucleotide molecule of claim 10 wherein said oligonucleotide molecule comprises a nucleotide sequence complementary to a nucleotide sequence of 5–50 nucleotides of SEQ ID NO:1.

12. The oligonucleotide molecule of claim 10 wherein said oligonucleotide molecule comprises a nucleotide sequence complementary to a nucleotide sequence of 10–40 nucleotides of SEQ ID NO:1.

13. The oligonucleotide molecule of claim 10 wherein said oligonucleotide molecule comprises a nucleotide sequence complementary to a nucleotide sequence of 15–25 nucleotides of SEQ ID NO:1.

14. The oligonucleotide molecule of claim 10 consisting of a nucleotide sequence complementary to a nucleotide sequence of at least 5–50 nucleotides of SEQ ID NO:1.

15. The oligonucleotide molecule of claim 14 consisting of a nucleotide sequence complementary to a nucleotide sequence of at least 18–28 nucleotides of SEQ ID NO:1.

* * * * *